(12) United States Patent
Fernandez et al.

(10) Patent No.: US 12,279,789 B2
(45) Date of Patent: Apr. 22, 2025

(54) CATHETER DEVICE WITH DETACHABLE DISTAL END

(71) Applicant: AVINGER, Inc., Redwood City, CA (US)

(72) Inventors: Anthony J. Fernandez, Castro Valley, CA (US); Richard R. Newhauser, Redwood City, CA (US); Himanshu N. Patel, San Jose, CA (US)

(73) Assignee: Avinger, Inc., Redwood City, CA (US)

( * ) Notice: Subject to any disclaimer, the term of this patent is extended or adjusted under 35 U.S.C. 154(b) by 327 days.

(21) Appl. No.: 17/747,715

(22) Filed: May 18, 2022

(65) Prior Publication Data

US 2022/0273336 A1   Sep. 1, 2022

Related U.S. Application Data

(63) Continuation of application No. 16/305,136, filed as application No. PCT/US2017/035510 on Jun. 1, 2017, now Pat. No. 11,344,327.
(Continued)

(51) Int. Cl.
*A61B 17/3207* (2006.01)
*A61B 17/00* (2006.01)
(Continued)

(52) U.S. Cl.
CPC . *A61B 17/320783* (2013.01); *A61M 25/0068* (2013.01); *A61B 2017/00473* (2013.01);
(Continued)

(58) Field of Classification Search
CPC .. A61B 17/320783; A61B 2017/00473; A61B 2017/320064; A61B 2017/320791; A61M 25/0068
See application file for complete search history.

(56) References Cited

U.S. PATENT DOCUMENTS 3,367,727 A   2/1968   Ward et al.
3,908,637 A   9/1975   Doroshow
(Continued)

FOREIGN PATENT DOCUMENTS

CN   1875242 A   12/2006
CN   1947652 A   4/2007
(Continued)

OTHER PUBLICATIONS

Smith et al.; U.S. Appl. No. 18/393,399 entitled "Chronic total occlusion crossing devices with imaging," filed Dec. 21, 2023.
(Continued)

*Primary Examiner* — Tan-Uyen T Ho
*Assistant Examiner* — Osama Nemer
(74) *Attorney, Agent, or Firm* — Shay Glenn LLP

(57) ABSTRACT

An atherectomy catheter includes an elongate catheter body, a cutter at a distal end of the catheter body, and a nosecone attached to a distal end of the catheter body. The cutter is configured to excise tissue from the body. The nosecone is configured to hold tissue excised from the cutter. The nosecone includes a distal section, a proximal section, and a connection mechanism that is configured to allow the distal section to attach and detach from the proximal section during use. The distal section includes a plug configured to sit within an inner diameter of the proximal section when the proximal section is connected to the distal section.

6 Claims, 20 Drawing Sheets

Related U.S. Application Data

(60) Provisional application No. 62/345,483, filed on Jun. 3, 2016.

(51) Int. Cl.
 *A61B 17/32* (2006.01)
 *A61M 25/00* (2006.01)

(52) U.S. Cl.
 CPC ............ *A61B 2017/320064* (2013.01); *A61B 2017/320791* (2013.01)

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,598,710 A | 7/1986 | Kleinberg et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,808,163 A | 2/1989 | Laub |
| 4,841,977 A | 6/1989 | Griffith et al. |
| 4,842,578 A | 6/1989 | Johnson et al. |
| 4,850,354 A | 7/1989 | Mcgurk-Burleson et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,002,560 A | 3/1991 | Machold et al. |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,217,479 A | 6/1993 | Shuler |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,449,372 A | 9/1995 | Schmaltz et al. |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,529,580 A | 6/1996 | Kusunok et al. |
| 5,556,405 A | 9/1996 | Lary |
| 5,607,394 A | 3/1997 | Andersen et al. |
| 5,613,981 A | 3/1997 | Boyle et al. |
| 5,620,426 A | 4/1997 | Braithwaite |
| 5,632,754 A | 5/1997 | Farley et al. |
| 5,632,755 A | 5/1997 | Nordgren et al. |
| 5,667,490 A | 9/1997 | Keith et al. |
| 5,674,232 A | 10/1997 | Halliburton |
| 5,676,012 A | 10/1997 | Ceriale |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,935,139 A | 8/1999 | Bates |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,217,549 B1 * | 4/2001 | Selmon ................. A61M 29/02 604/105 |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,009 B1 | 9/2002 | Dasilva et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |

(56) References Cited

U.S. PATENT DOCUMENTS

| | | |
|---|---|---|
| 6,485,413 B1 | 11/2002 | Boppart et al. |
| 6,497,649 B2 | 12/2002 | Parker et al. |
| 6,501,551 B1 | 12/2002 | Teamey et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,673,042 B1 | 1/2004 | Samson et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,776,062 B2 | 8/2010 | Besselink et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,213,224 B2 | 2/2019 | Guggenheimer et al. |
| 10,244,934 B2 | 4/2019 | Tachibana et al. |
| 10,314,667 B2 | 6/2019 | Garvey et al. |
| 10,335,173 B2 | 7/2019 | Carver et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,806,484 B2 | 10/2020 | Simpson et al. |
| 10,860,484 B2 | 10/2020 | Simpson et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |
| 11,076,773 B2 | 8/2021 | Patel et al. |
| 11,096,717 B2 | 8/2021 | Gupta et al. |
| 11,134,849 B2 | 10/2021 | Simpson et al. |

(56) References Cited

U.S. PATENT DOCUMENTS

| | | |
|---|---|---|
| 11,135,019 B2 | 10/2021 | Spencer et al. |
| 11,147,583 B2 | 10/2021 | Patel et al. |
| 11,206,975 B2 | 12/2021 | Tachibana et al. |
| 11,224,459 B2 | 1/2022 | Patel et al. |
| 11,278,248 B2 | 3/2022 | Christensen |
| 11,284,839 B2 | 3/2022 | Black et al. |
| 11,284,916 B2 | 3/2022 | Patel et al. |
| 11,344,327 B2 | 5/2022 | Fernandez et al. |
| 11,382,653 B2 | 7/2022 | Patel et al. |
| 11,399,863 B2 | 8/2022 | Patel et al. |
| 11,406,412 B2 | 8/2022 | Gupta et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0114875 A1 | 6/2003 | Sjostrom |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0163085 A1 | 8/2003 | Tanner et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1 | 1/2005 | Bonnette et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0149096 A1 | 7/2005 | Hilal et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0135763 A1 | 6/2007 | Musbach et al. |
| 2007/0167710 A1 | 7/2007 | Unal et al. |
| 2007/0196926 A1 | 8/2007 | Soito et al. |
| 2007/0213016 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |

(56) References Cited

U.S. PATENT DOCUMENTS

| | | |
|---|---|---|
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2008/0287795 A1 | 11/2008 | Klingensmith et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0073455 A1 | 3/2009 | Onimura |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0275966 A1 | 11/2009 | Mitusina |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0137140 A1 | 6/2011 | Tearney et al. |
| 2011/0144673 A1 | 6/2011 | Zhang et al. |
| 2011/0201924 A1 | 8/2011 | Teamney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0203230 A1 | 8/2012 | Adams |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0243881 A1 | 8/2014 | Lees et al. |
| 2014/0275996 A1 | 9/2014 | Stigall |
| 2014/0291985 A1 | 10/2014 | Cabrera et al. |
| 2014/0323800 A1 | 10/2014 | Dye |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0057690 A1* | 2/2015 | Simpson ........ A61B 17/320758 606/159 |
| 2015/0146211 A1 | 5/2015 | Bhagavatula et al. |
| 2015/0320975 A1 | 11/2015 | Simpson et al. |
| 2015/0327866 A1 | 11/2015 | Eckhouse et al. |
| 2016/0144155 A1 | 5/2016 | Simpson et al. |
| 2016/0310700 A1 | 10/2016 | Drake et al. |
| 2016/0354109 A1 | 12/2016 | Guggenheimer et al. |
| 2016/0354110 A1 | 12/2016 | Guggenheimer et al. |
| 2017/0100144 A1 | 4/2017 | Zhadkevich |
| 2017/0172666 A1 | 6/2017 | Govari et al. |
| 2017/0333674 A1 | 11/2017 | Walzman |
| 2018/0084985 A1 | 3/2018 | Saw et al. |
| 2018/0200488 A1 | 7/2018 | Drake et al. |
| 2018/0207417 A1 | 7/2018 | Zung et al. |
| 2018/0364024 A1 | 12/2018 | Baca et al. |
| 2019/0046230 A1 | 2/2019 | Smith et al. |
| 2019/0110809 A1 | 4/2019 | Rosenthal et al. |
| 2019/0313941 A1 | 10/2019 | Radjabi |
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/0267621 A1 | 9/2021 | Simpson et al. |
| 2021/0330345 A1 | 10/2021 | Newhauser et al. |
| 2021/0345903 A1 | 11/2021 | Patel et al. |
| 2022/0007941 A1 | 1/2022 | Kankaria |
| 2022/0031168 A1 | 2/2022 | Patel et al. |
| 2022/0039658 A1 | 2/2022 | Smith et al. |
| 2022/0039828 A1 | 2/2022 | Patel et al. |
| 2022/0071656 A1 | 3/2022 | Patel et al. |
| 2022/0079617 A1 | 3/2022 | Gupta et al. |
| 2022/0095926 A1 | 3/2022 | Simpson et al. |
| 2022/0125525 A1 | 4/2022 | Spencer et al. |
| 2022/0168011 A1 | 6/2022 | Patel et al. |

(56) References Cited

U.S. PATENT DOCUMENTS

| | | | |
|---|---|---|---|
| 2022/0183545 A1 | 6/2022 | Tachibana et al. | |
| 2023/0225616 A1 | 7/2023 | Patel et al. | |
| 2024/0057942 A1 | 2/2024 | Black et al. | |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| CN | 107530049 A | 1/2018 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |
| EP | 3446648 A1 | 2/2019 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011517601 A | 6/2011 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| JP | 2019512292 A | 5/2019 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO-2014142954 A1 * | 9/2014 ......... A61B 10/0275 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |
| WO | WO2017/007853 A1 | 1/2017 |
| WO | WO2017/132247 A1 | 8/2017 |
| WO | WO2017/161166 A1 | 9/2017 |
| WO | WO2018/094041 A1 | 5/2018 |

OTHER PUBLICATIONS

Simpson et al.; U.S. Appl. No. 18/416,264 entitled "Occlusion-crossing devices, imaging, and atherectomy devices," filed Jan. 18, 2024.
Patel et al.; U.S. Appl. No. 18/439,575 entitled "High speed chronic total occlusion crossing devices," filed Feb. 12, 2024.
Simpson et al.; U.S. Appl. No. 18/582,526 entitled "Identification of elastic lamina to guide interventional therapy," filed Feb. 20, 2024.
Patel et al.; U.S. Appl. No. 18/550,243 entitled "Occlusion-crossing devices," filed Sep. 12, 2023.
Patel; U.S. Appl. No. 18/480,452 entitled "Occlusion-crossing devices," filed Oct. 3, 2023.
Patel et al.; U.S. Appl. No. 17/816,673 entitled "Atherectomy catheter with serrated cutter," filed Aug. 1, 2022.
Aziz et al.; Chronic total occlusions—a stiff challenge requiring a major breakthrough: is there light at the end of the tunnel?; Heart; vol. 91; suppl. III; pp. 42-48; Jun. 2005.
Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vernelle.noel/Plastic_Snap_fit_design.pdf) on Sep. 26, 2018.
Choma et al.; Sensitivity advantage of swept source and fourier domain optical coherence tomography; Optics Express; 11(18); pp. 2183-2189; Sep. 8, 2003.
De Boer et al.; Improved signal-to-noise ratio in spectral-domain compared with time-domain optical coherence tomography; Optics Letters; 28(21); pp. 2067-2069; Nov. 2003.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Han et al.; In situ Frog Retina Imaging Using Common-Path OCT with a Gold-Coated Bare Fiber Probe; CFM6; San Jose, California; CLEO, May 4, 2008; 2 pages.
Leitgeb et al.; Performance of fourier domain vs time domain optical coherence tomography; Optics Express; 11(8); pp. 889-894; Apr. 21, 2003.

(56) References Cited

OTHER PUBLICATIONS

Linares et al.; Arbitrary single-mode coupling by tapered and nontapered grin fiber lenses; Applied Optics; vol. 29; No. 28; pp. 4003-4007; Oct. 1, 1990.

Merriam Webster; Proximal (Definition); 10 pages; retrieved from the internet (https://www.merriam-webster.com/dictionary/proximal) on Jun. 9, 2021.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

Sharma et al.; Common-path optical coherence tomography with side-viewing bare fiber probe for endoscopic optical coherence tomography; Rev. Sci. Instrum.; vol. 78; 113102; 5 pages: Nov. 6, 2007.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Wikipedia; Hinge; 4 pages; retrieved from the internet (https://en.wikipedia.org/w/index.php?title=Hinge&oldid=479569345) on Jun. 9, 2021.

Black et al.; U.S. Appl. No. 17/652,073 entitled "Optical coherence tomography for biological imaging," filed Feb. 22, 2022.

Patel et al.; U.S. Appl. No. 17/762,815 entitled "Atherectomy catheter with shapeable distal tip," filed Mar. 23, 2022.

Patel.; U.S. Appl. No. 17/763,810 entitled "Occlusion-crossing devices," filed Mar. 25, 2022.

Patel et al.; U.S. Appl. No. 17/749,882 entitled "Atherectomy Catheter," filed May 20, 2022.

Rosenthal et al.; U.S. Appl. No. 18/337,852 entitled "Atherectomy catheter with laterally-displaceable tip," filed Jun. 20, 2023.

Patel.; U.S. Appl. No. 18/716,831 entitled "Atherectomy catheter with shapeable distal tip," filed Jun. 5, 2024.

\* cited by examiner

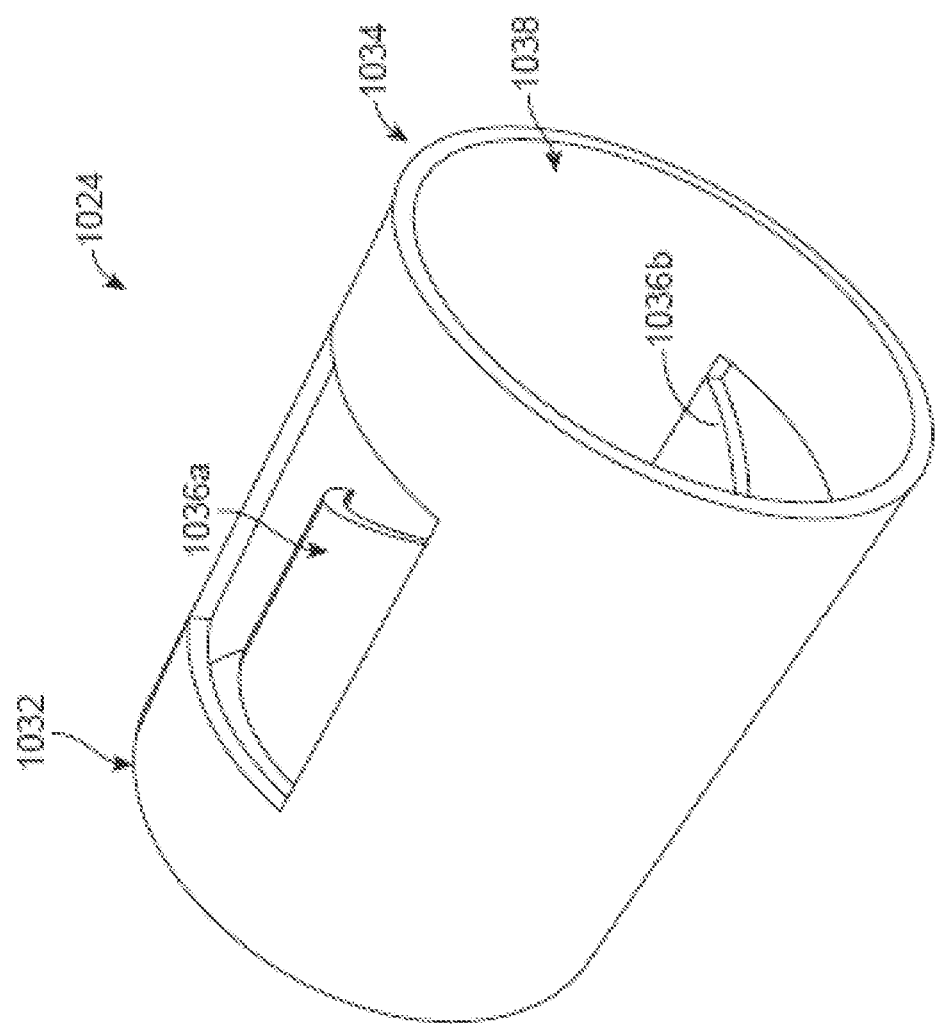

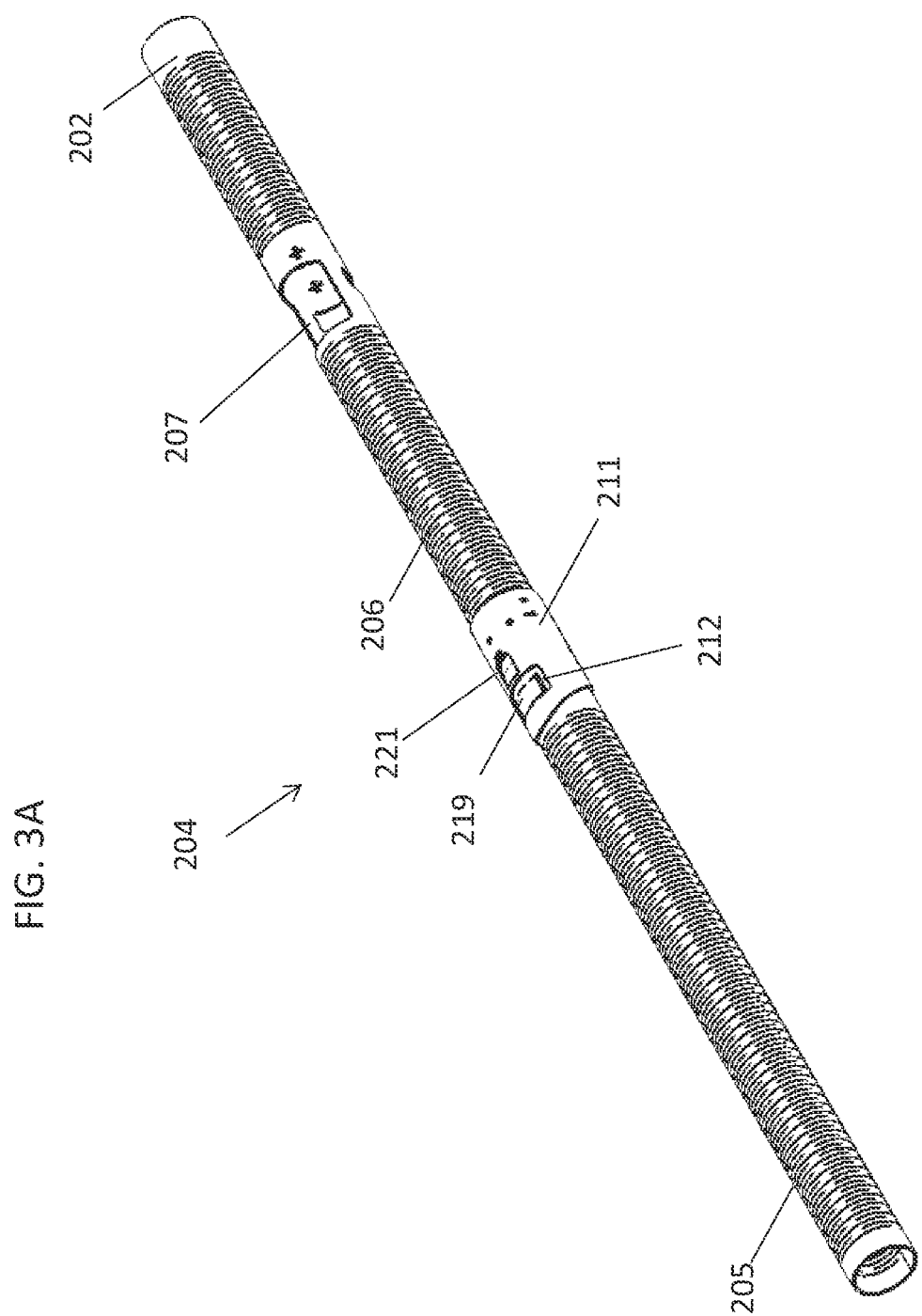

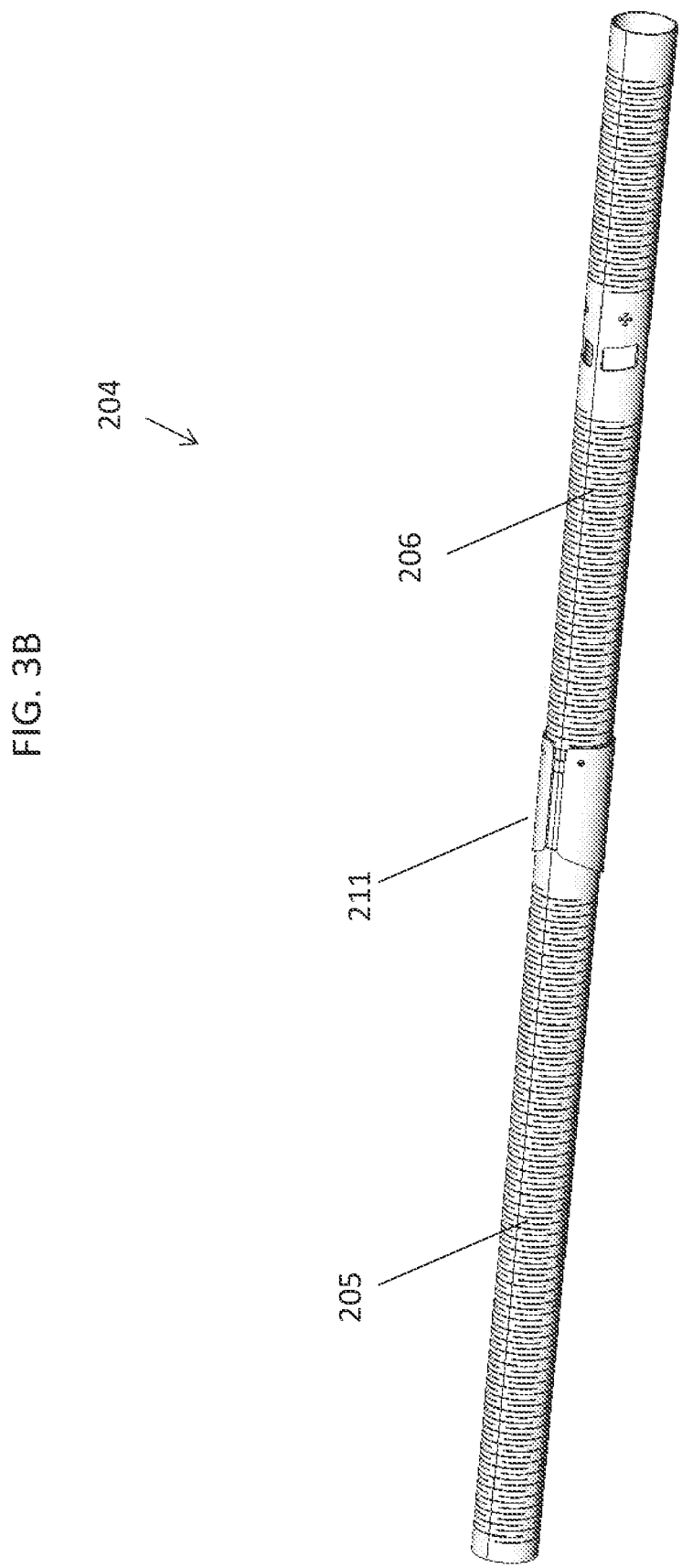

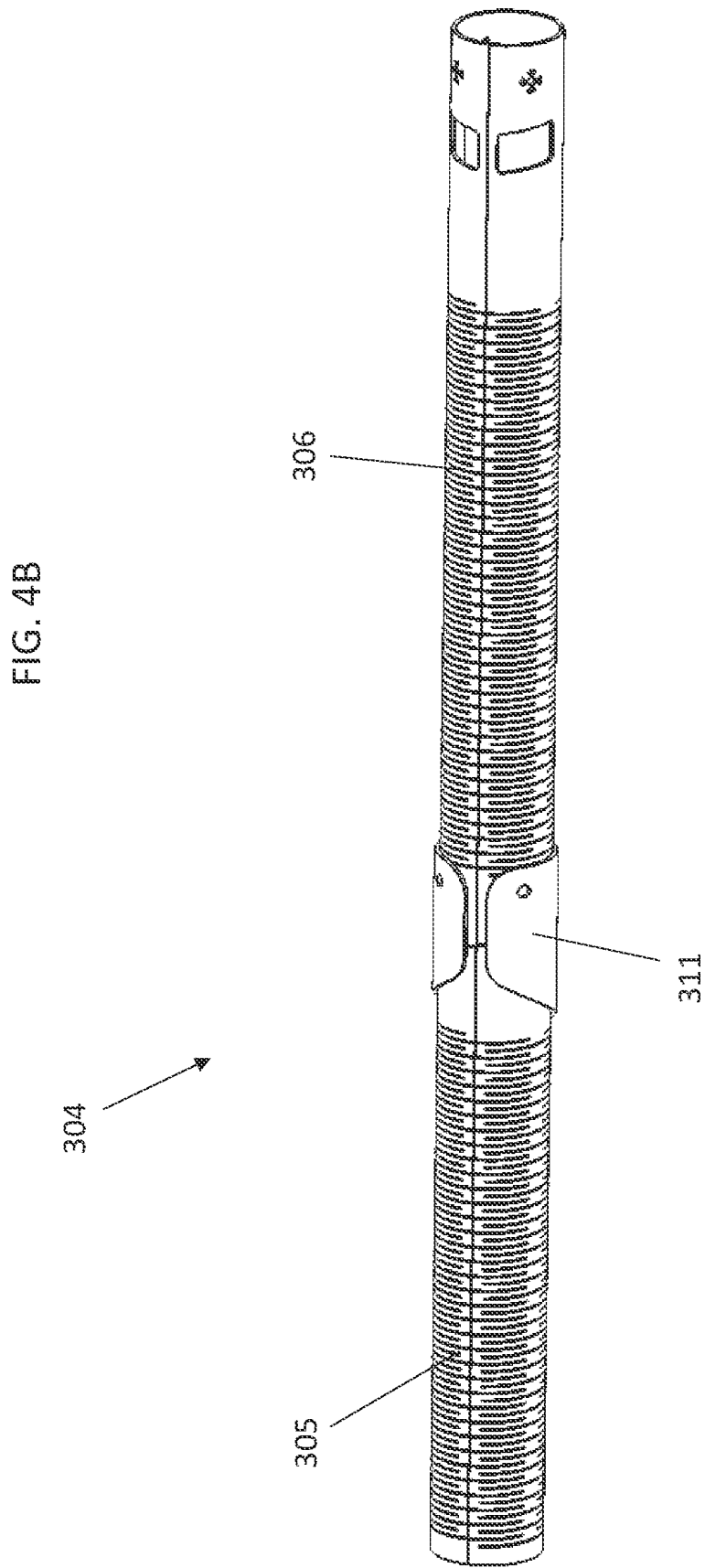

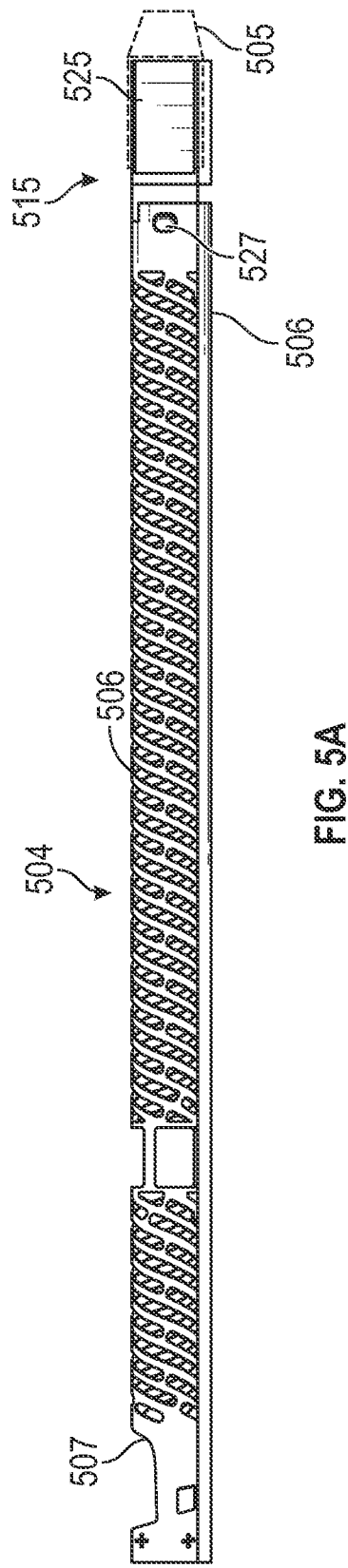
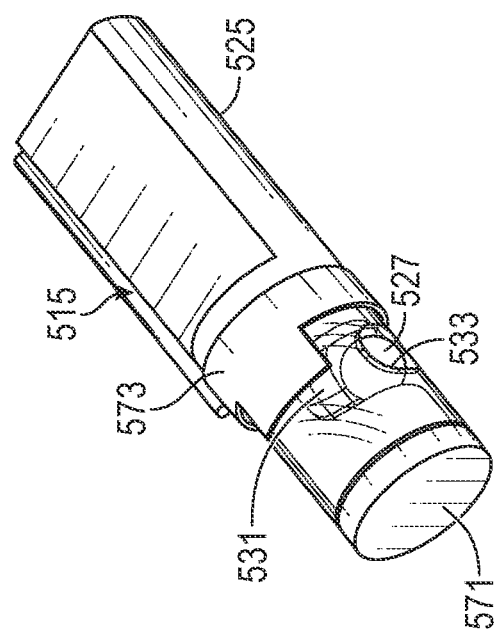
FIG. 5A
FIG. 5B

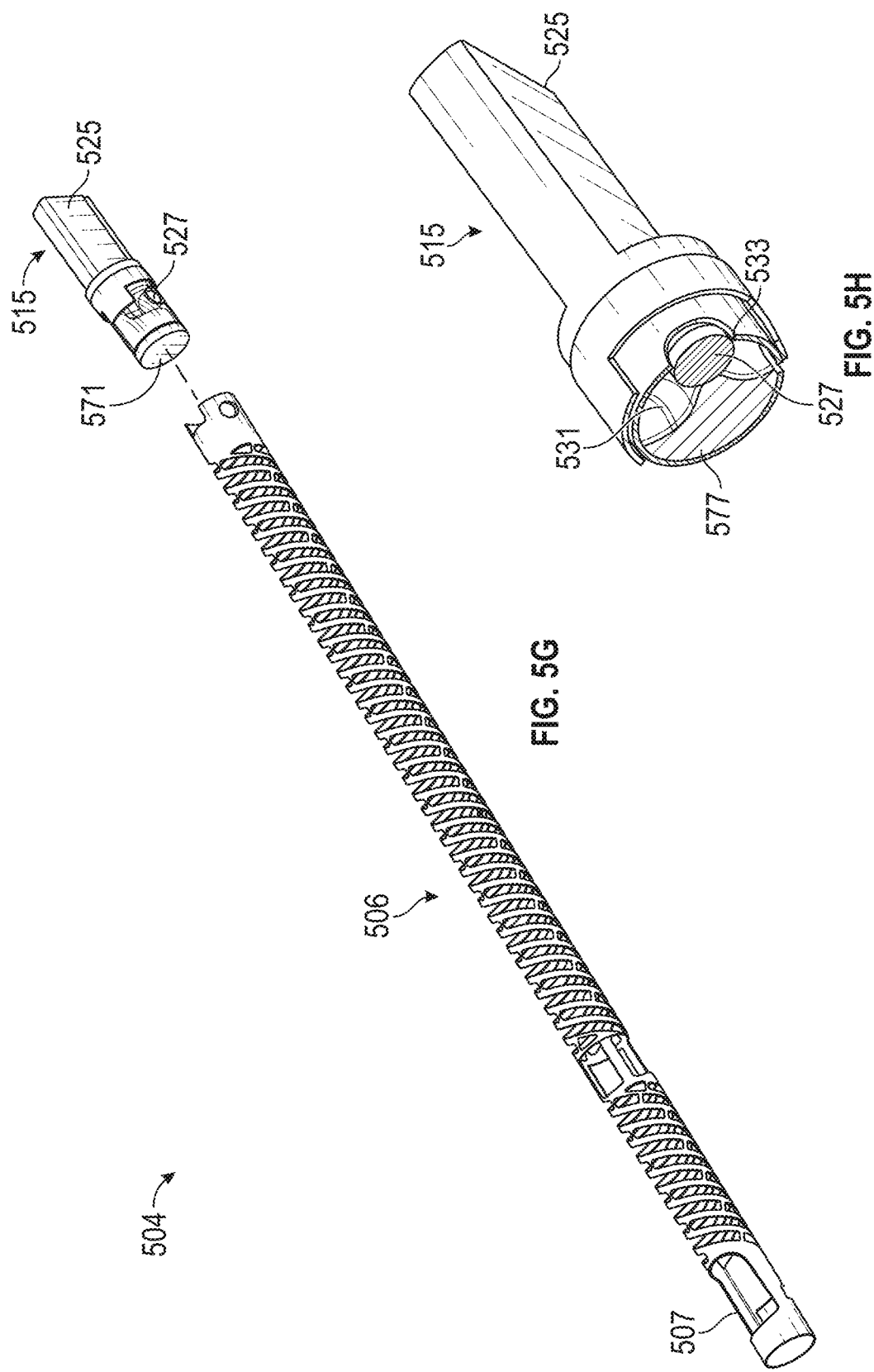

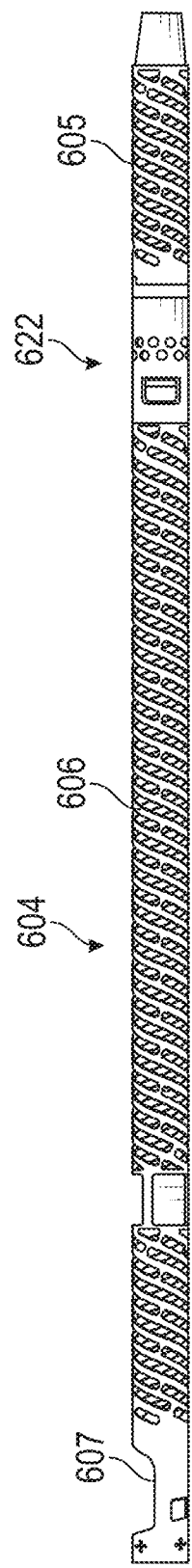
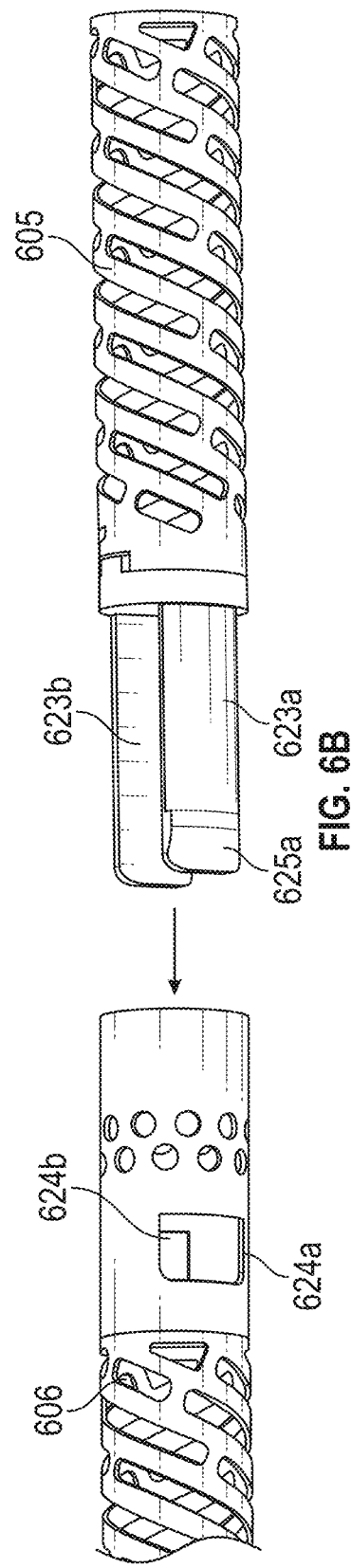
FIG. 6A
FIG. 6B

CATHETER DEVICE WITH DETACHABLE DISTAL END

CROSS REFERENCE TO RELATED APPLICATIONS

This application is a continuation of U.S. patent application Ser. No. 16/305,136, filed on Nov. 28, 2018, and titled "CATHETER DEVICE WITH DETACHABLE DISTAL END," now U.S. Patent Application Publication No. 2020/0323553, which is the U.S. National Stage Entry of International Patent Application No. PCT/US2017/035510, filed on Jun. 1, 2017, and titled "CATHETER DEVICE WITH DETACHABLE DISTAL END," which claims priority to U.S. Provisional Patent Application No. 62/345,483, filed Jun. 3, 2016, and titled "DETACHING NOSECONE FOR CATHETER DEVICE," the entirety of which is incorporated by reference herein.

This application may be related to PCT Application WO 2014/142954 entitled, "TISSUE COLLECTION DEVICE FOR CATHETER" filed on Mar. 15, 2013, which is herein incorporated by reference in its entirety. This application may also be related to U.S. patent application Ser. No. 13/175,232, filed Jul. 1, 2011, titled "ATHERECTOMY CATHETERS WITH LONGITUDINALLY DISPLACEABLE DRIVE SHAFTS," now U.S. Pat. No. 9,345,510, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application is related to tissue collection devices that can be used with occlusion-crossing devices or systems such as atherectomy catheters. In particular, described herein are nosecones that can be used with catheter devices where the connection does not interfere with the catheter device cutter and its function of cutting and clearing out debulked tissue.

BACKGROUND

Peripheral artery disease (PAD) affects millions of people in the United States alone. PAD is a silent, dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for PAD may include endarterectomy and/or atherectomy. Atherectomy offers a simple mechanical advantage over alternative therapies. Removing the majority of plaque mass (e.g., debulking) may create a larger initial lumen and dramatically increases the compliance of the arterial wall. As a result, stent deployment is greatly enhanced.

While atherectomy may provide a minimally invasive solution to clearing the way for placement of stents within initially blocked arteries, there remains a need to improve certain aspects of atherectomy catheters presently available. For example, tissue collection and/or tissue removal from the arteries is a common challenge during atherectomy procedures. One mechanism for handling debulked tissue is to collect the tissue in a distal nosecone or collection chamber of the device. However, removing the tissue from the collection chamber or cleaning the chamber remains difficult. Accordingly, an atherectomy catheter that addresses some of these problems is desired.

SUMMARY OF THE DISCLOSURE

In general, in one embodiment, an atherectomy catheter includes an elongate catheter body, a cutter at a distal end of the catheter body, and a nosecone attached to a distal end of the catheter body. The cutter is configured to excise tissue from the body. The nosecone is configured to hold tissue excised from the cutter. The nosecone includes a distal section, a proximal section, and a connection mechanism that is configured to allow the distal section to attach and detach from the proximal section during use. The distal section includes a plug configured to sit within an inner diameter of the proximal section when the proximal section is connected to the distal section.

This and other embodiments can include one or more of the following features. The nosecone can further include a hollow interior portion configured to receive excised tissue. The nosecone can be flexible. The atherectomy catheter can further include a guidewire channel disposed along an exterior of the nosecone. The guidewire channel can include a distal portion extending along the distal section of the nosecone and a proximal portion extending along the proximal section of the nosecone. The distal portion and proximal portion can be configured to align when the proximal section and the distal section are connected together. The distal portion and proximal portions can be configured to prevent the proximal section and distal sections from rotating relative to one another when a guidewire is placed therethrough. The connection mechanism can further include a tab configured to be gripped through the distal section of the nosecone to rotate the distal section relative to the proximal section to activate or deactivate the connection mechanism. The connection mechanism can further include a cam and ball bearing configured to lock and unlock the proximal section relative to the distal section. The connection mechanism can include a plurality of snap arms configured to extend into the proximal section and to interlock with apertures on the proximal section. The snap arms can each include a tab configured to fit within the apertures. The tabs can be chamfered along a side edge such that rotation of the distal section towards the chamfered edges causes the distal section to automatically unlock from the proximal section. The nosecone can be configured to pivot away from the elongate catheter body to further expose the cutter. The cutter can be configured to move axially into the nosecone to pack tissue.

In general, in one embodiment, an atherectomy catheter includes a catheter body having a catheter body proximal end, a catheter body distal end, a cutting window, a cutter exposable through the cutting window, a nosecone, and a collar. A nosecone has a nosecone proximal end and a nosecone distal end. The nosecone proximal end is configured to couple and decouple from the nosecone distal end. The collar has a collar inner surface configured to maintain a detachable connection between the nosecone proximal end with the nosecone distal end.

This and other embodiments can include one or more of the following features. The nosecone can further include a hollow interior portion configured to receive excised tissue. The atherectomy catheter can further include a locking mechanism for maintaining connection between the nosecone proximal end with the nosecone distal end. The locking mechanism components can be disposed on the nosecone proximal end, the collar, the nosecone distal end, or a combination thereof. The locking mechanism can utilize corresponding threads for mating the detachable nosecone proximal end to the nosecone distal end. The locking mechanism can utilize at least one tab and corresponding aperture for mating the detachable nosecone distal end to the nosecone proximal end. The locking mechanism may not interfere with cutter's ability to extend past the locking mechanism. The nosecone can be rigid. The nosecone can be flexible. The nosecone can include both flexible and rigid regions. The atherectomy catheter can further include a guidewire channel disposed on the nosecone and the catheter body.

In general, an atherectomy catheter includes a catheter body having a catheter body proximal end, a catheter body distal end, a cutting window, a cutter exposable through the cutting window, a nosecone, a collar, and a locking mechanism for maintaining connection between the proximal and distal ends of the nosecone. A nosecone has a nosecone proximal end and a nosecone distal end. The nosecone proximal end is configured to couple and decouple from the nosecone distal end. The collar is configured to maintain connection between the nosecone proximal end with the nosecone distal end. The locking mechanism components are disposed on the nosecone proximal end, the collar, the nosecone distal end, or a combination thereof.

This and other embodiments can include one or more of the following features. The nosecone can further include a hollow interior portion configured to receive excised tissue. The locking mechanism can utilize corresponding threads for mating the nosecone proximal end with the nosecone distal end. The locking mechanism can utilize at least one tab and corresponding aperture for mating the nosecone proximal end with the detachable nosecone distal end. The locking mechanism cannot interfere with the cutter's ability to extend past the locking mechanism. The nosecone can be rigid. The nosecone can be flexible. The nosecone can include both flexible and rigid regions.

In general, an atherectomy catheter includes a catheter body having a catheter body proximal end, a catheter body distal end, a cutting window, a cutter exposable through the cutting window, a nosecone, a collar, and a locking mechanism for maintaining connection between the detachable nosecone and the catheter body. A nosecone has a nosecone proximal end and a nosecone distal end. The nosecone proximal end is configured to couple and decouple from the nosecone distal end. The collar is configured to maintain connection between the detachable nosecone and the catheter body. The locking mechanism includes corresponding threads on the collar, nosecone proximal end, or nosecone distal end adapted to couple the proximal and distal ends of the nosecone.

In general, in one embodiment, an atherectomy catheter includes a catheter body having a catheter body proximal end, a catheter body distal end, a cutting window, a cutter exposable through the cutting window, a nosecone, a collar, and a locking mechanism for maintaining connection between the proximal and distal ends of the nosecone. A nosecone has a nosecone proximal end and a nosecone distal end. The nosecone proximal end is configured to couple and decouple from the nosecone distal end. The collar is configured to maintain connection between the detachable nosecone and the catheter body. The locking mechanism includes at least one tab disposed on the collar having corresponding aperture adapted to mate the proximal and distal ends of the nosecone.

This and other embodiments can include one or more of the following features. The atherectomy catheter can further include a drive system configured to extend and retract the cutter within the nosecone.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1E and 1F shows a perspective view of a second coupling element of the coupling mechanism of FIG. 1B.

FIG. 2A shows a coupling element including two tabs. FIG. 2B shows a coupling element including to corresponding apertures and configured to lock with the coupling element of FIG. 2A.

FIG. 3A shows a top perspective view of a portion of an atherectomy catheter having a nosecone with a detachable distal end that is connected through a single tab coupling mechanism.

FIG. 3B shows a bottom perspective view of the portion of the atherectomy catheter of FIG. 3A.

FIG. 4B shows a bottom view of the portion of the nosecone of FIG. 4A.

FIG. 5A shows an exemplary nosecone having a detachable distal end activated by a cam and ball mechanism.

FIG. 5B shows the cam and ball mechanism.

FIG. 5G shows the nosecone of FIG. 5A with the distal end detached from the proximal end.

FIG. 5H shows a cross-section through FIG. 5B to more clearly show the cam path.

FIG. 6A shows an exemplary nosecone having a detachable distal end activated by a snap mechanism.

FIG. 6B shows the proximal and distal ends disconnected.

DETAILED DESCRIPTION

Described herein are atherectomy catheters including an elongate body, a cutter, and a nosecone configured to collect debulked tissue. The nosecone includes an atraumatic distal end, a proximal end that couples to the remainder of the catheter body, and an interior region for collecting excised tissue. The proximal portion of the nosecone is detachable from the distal portion for ease of cleaning and/or for quick replacement of the distal portion of the nosecone during an atherectomy procedure.

The nosecones described herein include features that both allow easy coupling of the proximal and distal ends of the nosecone and prevent unwanted decoupling during use. Moreover, the interior surface of the nosecone with detachable distal/proximal portions can be substantially smooth, allowing a cutter to extend therein (e.g., to pack tissue) without hindrance.

Figure 1A:
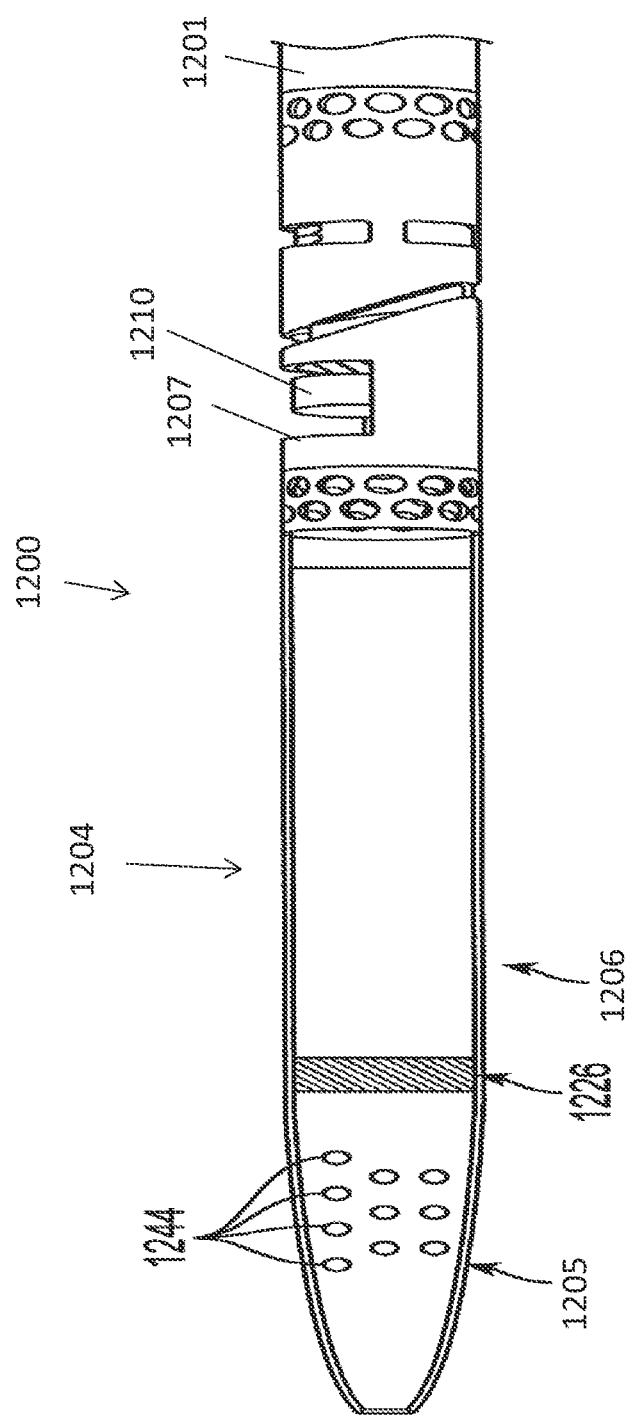
FIG. 1A shows a distal end of an atherectomy catheter having a tissue connection nosecone with a detachable distal end.

The distal end of an exemplary atherectomy catheter 1200 is shown in FIG. 1A. The atherectomy catheter includes a catheter body 1201, a hollow nosecone 1204, an annular rotatable cutter 1210, and a cutter window 1207 through which the cutter can debulk tissue. The hollow nosecone 1204 can be configured to collect tissue as it is removed in the body. Further, in some embodiments, the cutter 1210 can be moved axially into the nosecone 1204 to pack tissue therein. Moreover, in some embodiments, the nosecone 1204 can hinge relative to the catheter body 1201, such as at a pivot point. As shown in FIG. 1A, in some embodiments, the nosecone can include holes 1244 therein for venting. A distal section or end 1205 of the nosecone 1204 can be configured to detach from the proximal portion 1206 of the nosecone 1204 at attachment/detachment point 1226 to allow for ease of removing collected or packed tissue. The attachment/detachment point 1226 can include, for example, one or more coupling elements. Various embodiments of coupling elements are described herein.

FIGS. 1B-1F show an exemplary coupling mechanism 111 that includes a first coupling element 925 configured to interface with a corresponding coupling element 1024 for locking and unlocking of the proximal and distal portions of a nosecone (such as nosecone 1204).

Figure 1B:
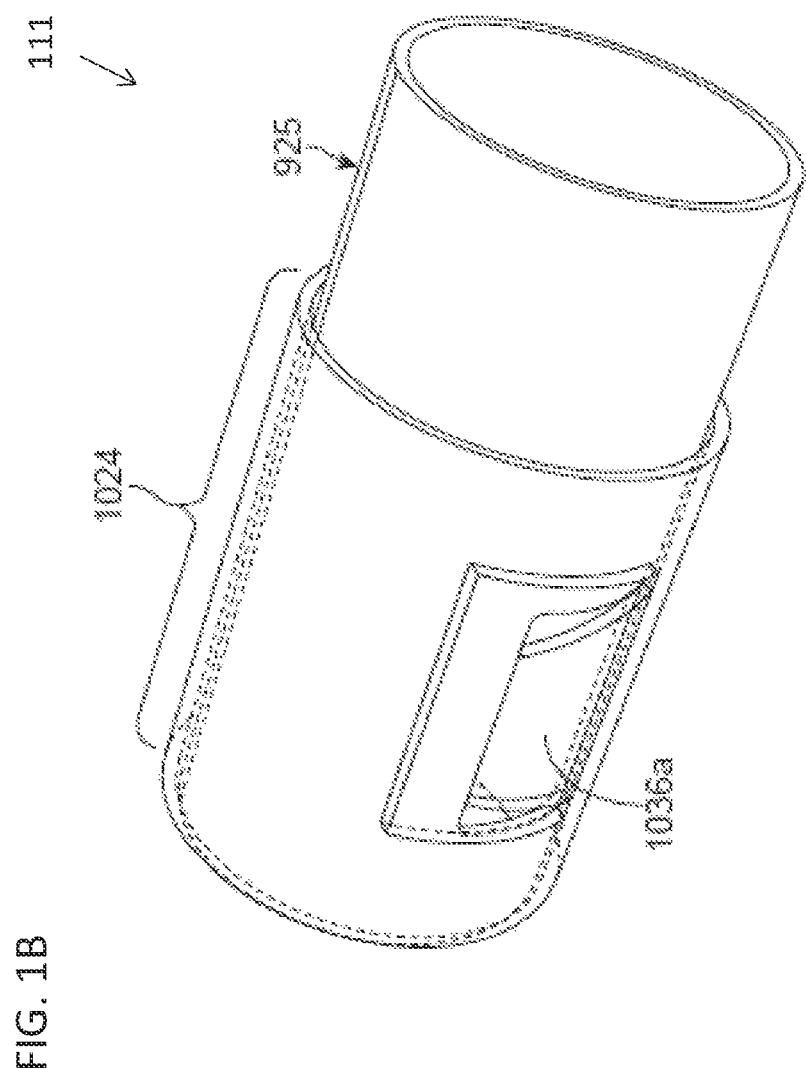
FIG. 1B is a perspective view of an exemplary coupling mechanism for coupling detachable proximal and distal sections of a nosecone.
Figure 1C:
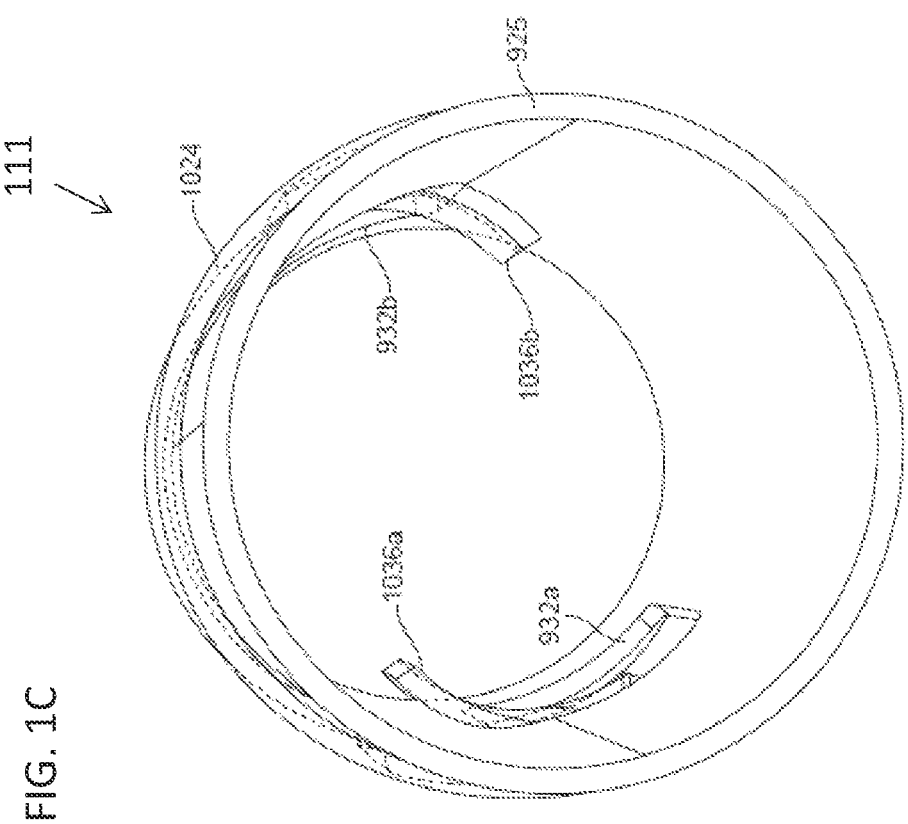
FIG. 1C shows a cross-section of the coupling mechanism of FIG. 1B.
Figure 1D:
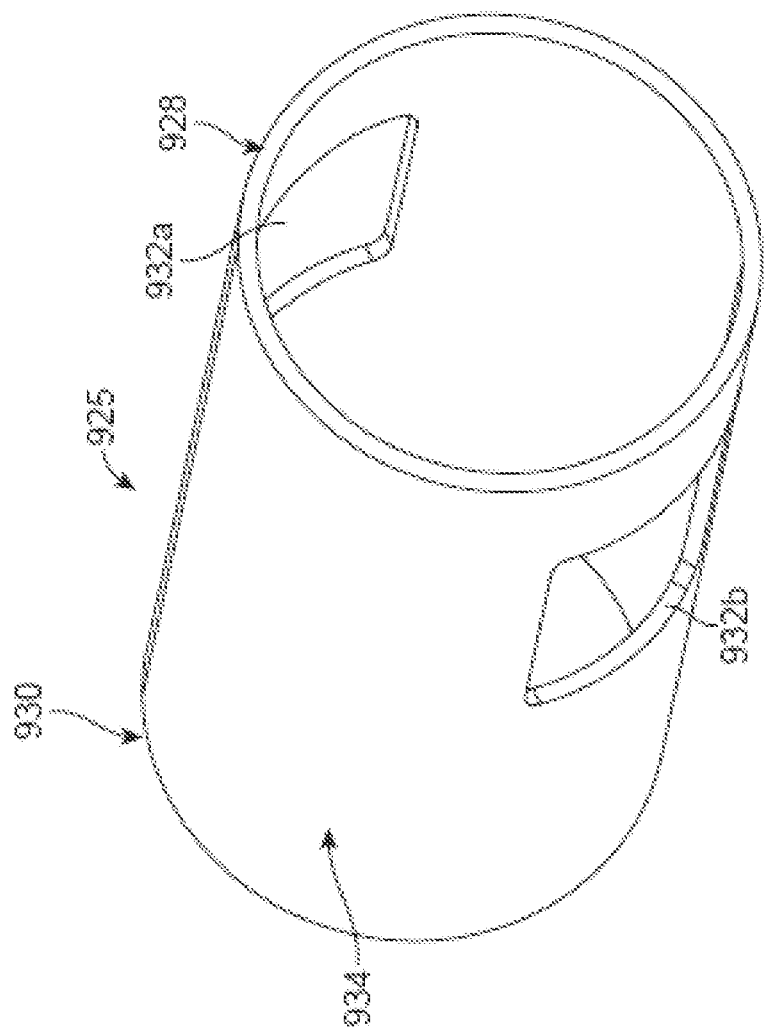
FIG. 1D is a perspective views of a first coupling element of the coupling mechanism of FIG. 1B.

FIG. 1D shows the coupling element 925, which includes a proximal end 930 and a distal end 928. The coupling element 925 includes a generally cylindrical main body with a lumen between the proximal and distal ends. The slots or cutouts 932a-b are formed through the wall of the main body. Although shown with two slots having a generally rectangular shape, the coupling element 925 can have any number of slots with any shape. The shape of the main body is designed to be inserted into the corresponding coupling element 1024 for attachment.

Figure 1F:
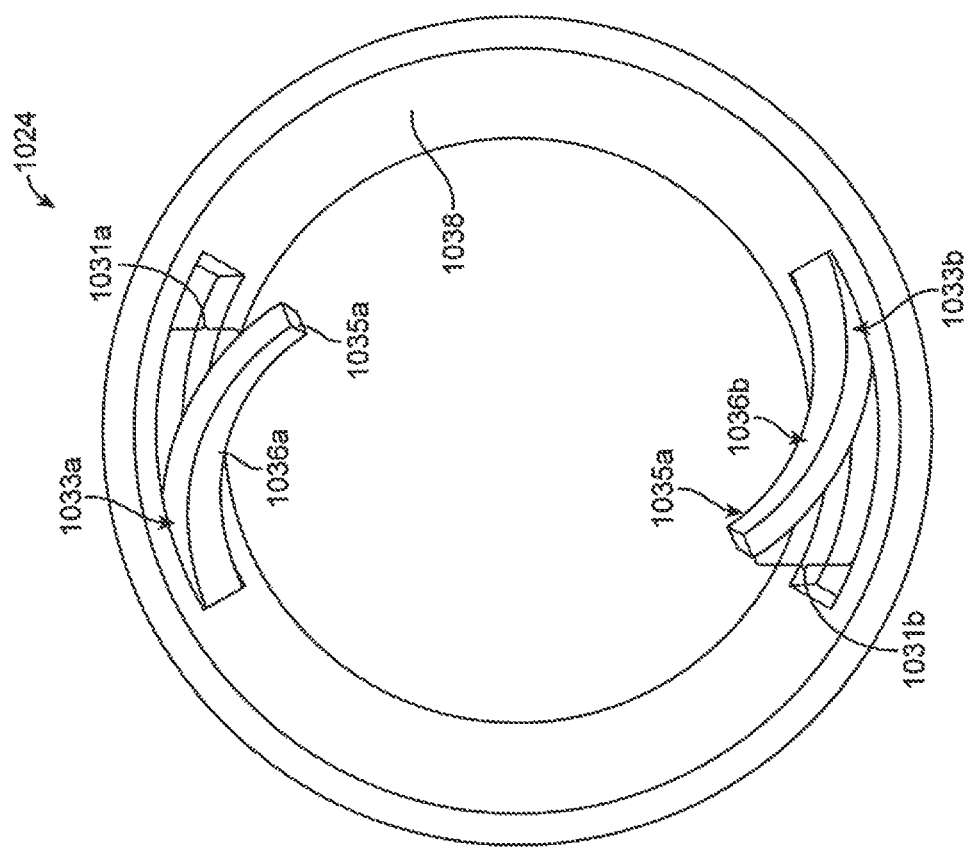

FIGS. 1E and 1F illustrate the corresponding coupling element 1024 that is configured to releasably attach to the coupling element 925. The corresponding coupling element 1024 is shape set to the coupling element 925 such that coupling element 925 can be inserted into the corresponding coupling element 1024 to form a snug fit (as shown in FIGS. 1B-1C). The corresponding coupling element 1024 has an inner wall 1038 that contacts the outer wall 934 of the coupling element 925 when fitted. Further, the corresponding coupling element 1024 includes protrusions shown as tabs 1036a-b that project from its main body towards the center. In some embodiments, the tabs 1036a-b protrude at an angle towards the center of the main body between the proximal end 1032 and the distal end 1034 and are configured to extend into the receiving slots 932a-b.

Thus, in operation, the corresponding coupling element 1024 is placed over the outer wall 934 of the coupling element 925. The proximal end 1032 of the corresponding coupling element 1024 is advanced over the distal end 928 of the coupling element 925. Then the corresponding coupling element 1024 (or the coupling element 925) is rotated relative to the other element to align the tabs 1036a-b with the slots 932a-b. To lock the coupling elements, an edge of the slots 932a-b is slid into the recess 1031a-b until a portion of the main body of the coupling element 925 is held between a tab surface and the inner wall of the corresponding coupling element 1024. FIGS. 1B-1C shows the corresponding coupling element 1024 surrounding the coupling element 925 with tabs 1036a-b engaged with slots 932a-b. The tabs 1036a-b are received through the slots 932a-b into an interior of the coupling element 925. The edge of the slots 932a-b are slid into the recesses 1031a-b to hold and lock the lateral orientation of the coupling element 925 within the corresponding coupling element 1024. As shown, rotating the corresponding coupling element counter-clockwise disengages the coupling elements and releases the coupling elements from one another.

Figure 2A:
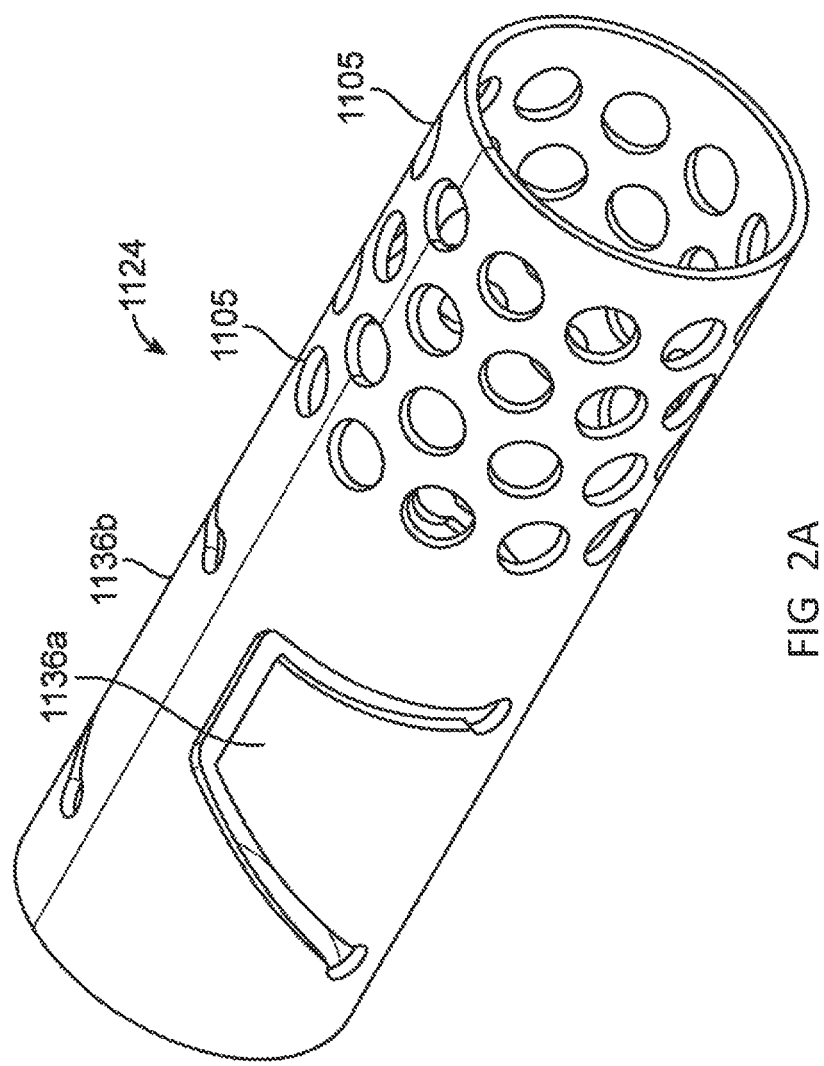
FIGS. 2A and 2B show an alternative exemplary coupling mechanism for a nosecone.
Figure 2B:
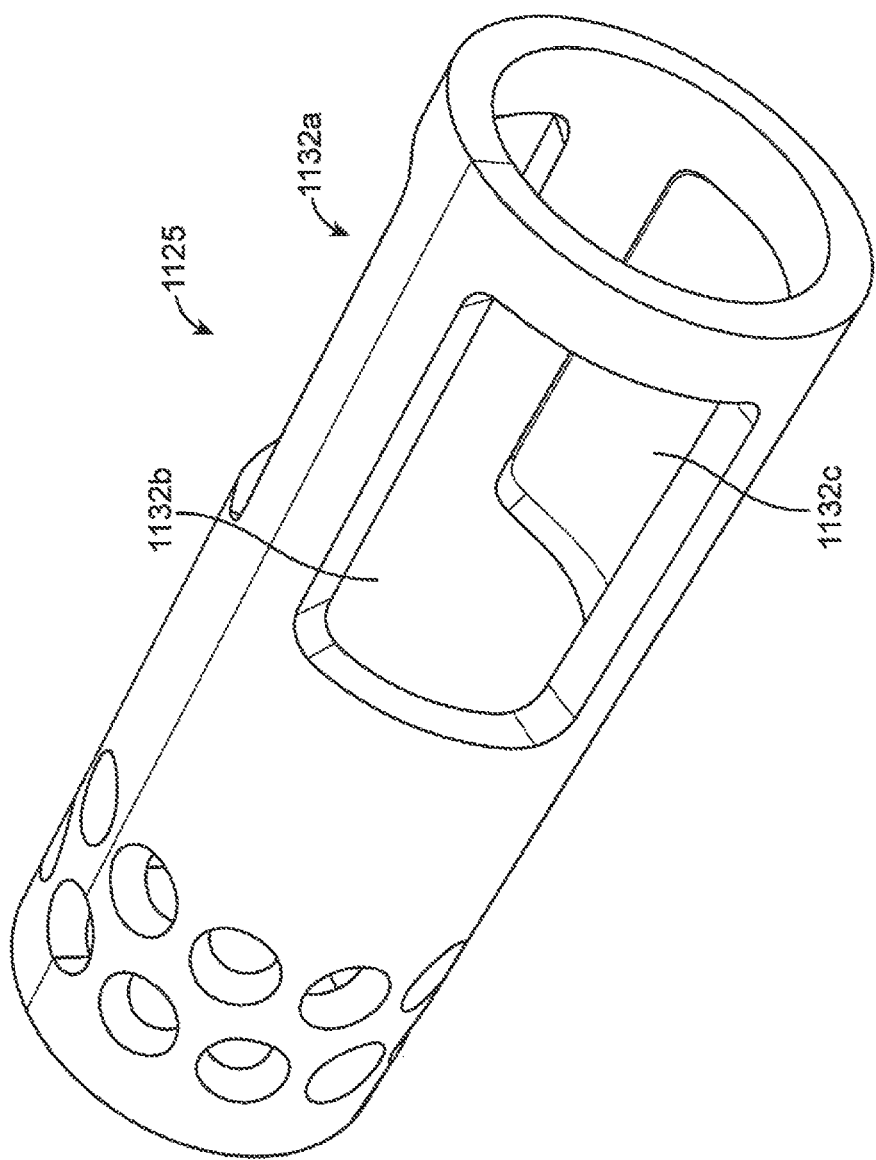

FIGS. 2A and 2B show variations of the coupling elements shown in FIGS. 1B-1F. For example, FIG. 2A shows a corresponding coupling element 1124 with two tabs 1136a-b and a plurality of apertures 1105. In some embodiments, the apertures provide for fluid pressure release. FIG. 2B shows a coupling element 1125 having slots 1132a-c, e.g., configured to interact with tabs 1136a-b of FIG. 2A. Although the coupling elements of FIGS. 1B-1F and 2A-2B are shown with two or three tabs/slots, it is to be understood that any number of mating structures can be used to form the detachable tissue collection devices.

FIG. 3A shows another embodiment of a nosecone 204 that can be used with an atherectomy catheter. The nosecone 204 includes a distal end 205 that is detachable from a proximal end 206 at coupling mechanism 211. The nosecone distal end 205 is atraumatic.

The nosecone 204 further includes a cutting aperture 207 that allows cutter (e.g., an annular cutter) of the device to be exposed therethrough for cutting and removing tissue. The nosecone proximal end 206 is configured to couple with the remainder of the catheter body, such as at a connection point 202. For example, the catheter body 1201 can be coupled with the nosecone 204 proximal to the cutting aperture 207. In some embodiments, the nosecone 204 can be connected at a hinge point so as to hinge away from the catheter body.

Referring to FIGS. 3A and 3B, the coupling between the nosecone 204 distal end 205 and proximal end 206 may include a collar 211. The collar 211, in turn, may be attached permanently to the nosecone proximal end 206 as shown. The collar 211 can include a collar aperture 212 that is able to couple to a corresponding feature (e.g. a tab 219 or other protrusion) on the proximal end 206 of the nosecone 204. The tab 219 can be configured to include an amount of flexibility such that a user is able to push the end of the collar 211 past the tab 219 to align the tab 219 and the collar aperture 212. The insertion of the distal end 205 into the collar 211 can be aided by the angled or beveled distal edge of the collar 211.

Once aligned with the collar aperture 212, the tab 219 can be engaged or locked within the aperture 212 by an extension 221 on the collar 211. The extension 221 is configured to contact the tab 219, causing the tab 219 to pivot (e.g., at a flexion point) with the proximal end of the tab 219 moving radially towards the central axis of the collar 211 and the distal end of the tab 219 moving radially away from the central axis of the collar 211 to engage/attach within the collar aperture 212 and lock the tab 219 in place. Once the tab 219 is locked in place, the proximal and distal ends 206, 205 of the nosecone will then be connected and/or locked together. To disengage the collar 211 from the distal end 205 of the nosecone 204, the user can push on the tab to free the tab from the collar aperture 212 and slide the collar 211 axially away from the distal end 205 of the nosecone 204.

In an alternative embodiment, the collar 211 may be permanently attached to the distal end 205 of the nosecone 204 rather than the proximal end 206. Here, the proximal end 206 of the nosecone 204 may include corresponding features with the collar 211 including tabs with corresponding apertures that are able to mate, corresponding threads that screw together, etc.

In some other variations, the collar 211 may be completely detachable from both the nosecone proximal end 206 and the nosecone distal end 205. In this design, the collar 211 may have two or more coupling features for mating the nosecone proximal end 206 to the nosecone distal end 205. The coupling features on the collar 211 in this example may also be used to properly align the nosecone proximal end 206 with the nosecone distal end 205. For example, the collar may have tabs that mate with corresponding tab acceptors on both the nosecone distal end 205 and the nosecone proximal end 206 for holding the two components together, but in addition, the collar 211 may also have additional features that aid with ensuring that the nosecone distal end 205 is properly aligned with the nosecone proximal end 206. These additional features may include, but are not limited to, protrusions and corresponding apertures or slots.

Figure 4A:
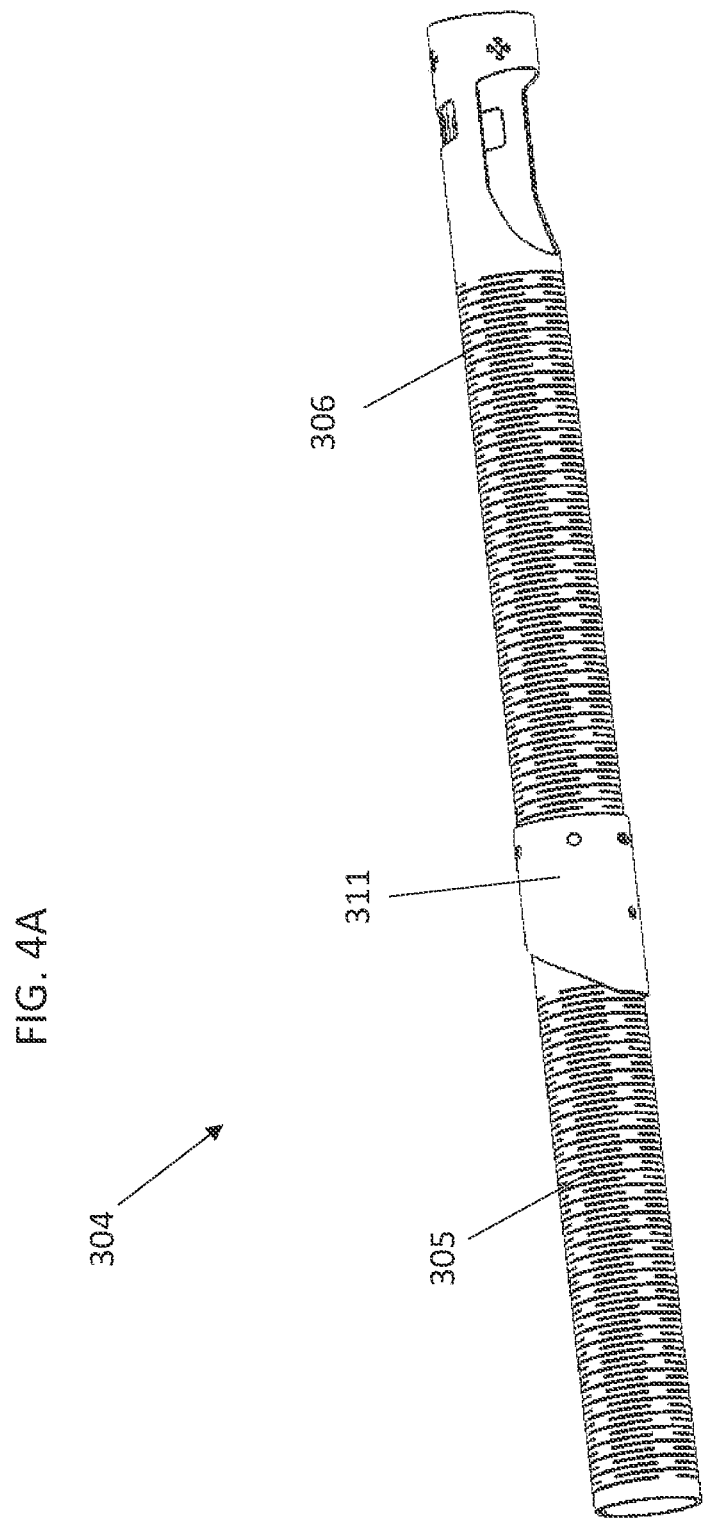
FIG. 4A shows a side perspective view of a portion of a nosecone with a detachable distal end that is connected through a twist mechanism.
Figure 4C:
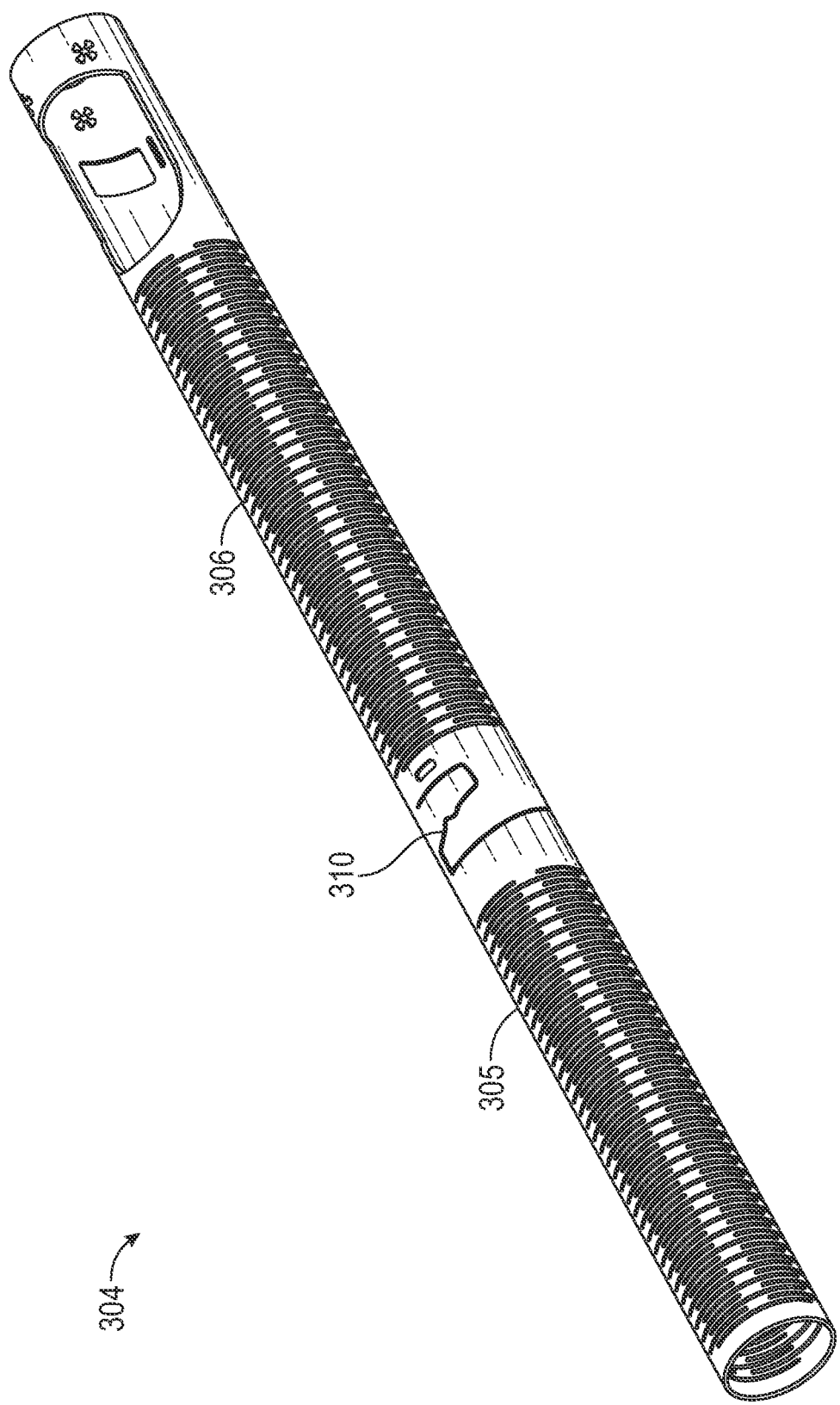
FIG. 4C-4E show the nosecone of FIG. 4A with the collar removed so as to make the twist/aligning features between the proximal and distal ends visible.
Figure 4D:
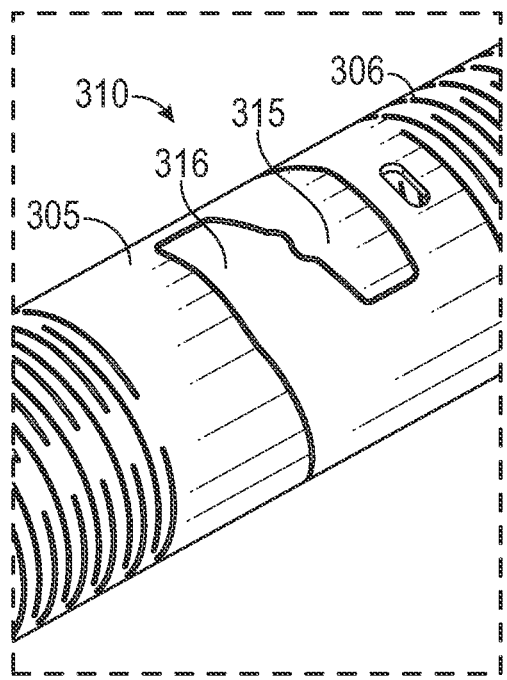
Figure 4E:
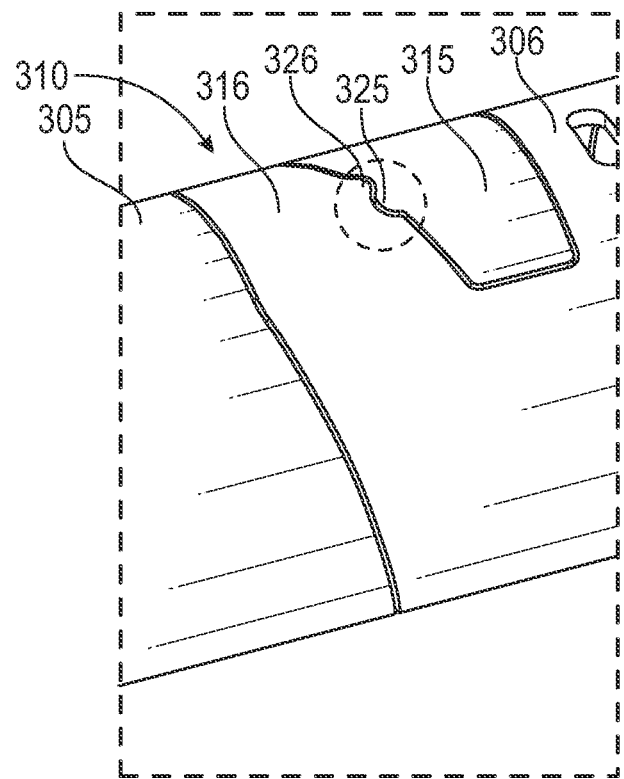

Turning to FIGS. 4A-4E, another coupling mechanism 310 between the distal end 305 and proximal end 306 of a nosecone 304 is shown. The coupling mechanism 310 for the nosecone 304 employs a twist type motion to engage and disengage the nosecone distal end 305 with the nosecone proximal end 306. The twist coupling mechanism 310 is best shown in FIGS. 4C-4E (the collar 311 has been removed in these figures for clarity). The twist coupling mechanism 310 includes a hooked, curved, or c-shaped extension 315 on the distal end 305 that interlock or mates with a corresponding hooked, curved, or c-shaped extension 316 on the proximal end 306 when the proximal and distal ends 306, 305 are rotated relative to one another. Each extension 315, 316 includes a wave-like curve or bump 326, 325 that fits with the corresponding bump 326, 325 on the opposite side. To connect the proximal and distal portions 306, 305, the two portions can be rotated relative to one another. To release, they can be rotated in the opposite direction.

Referring back to FIGS. 4A-4B, the collar 311 can be clamped over the twist mechanism 310 to keep the extensions 315, 316 from rotating apart during use. The collar 311 can be permanently attached to either the proximal end (as shown in FIGS. 3A-3B) or the distal end. When attached to the proximal end, the collar 311 can have a beveled or angled distal edge to aid in insertion of the distal end 305 therein.

Figure 5C:
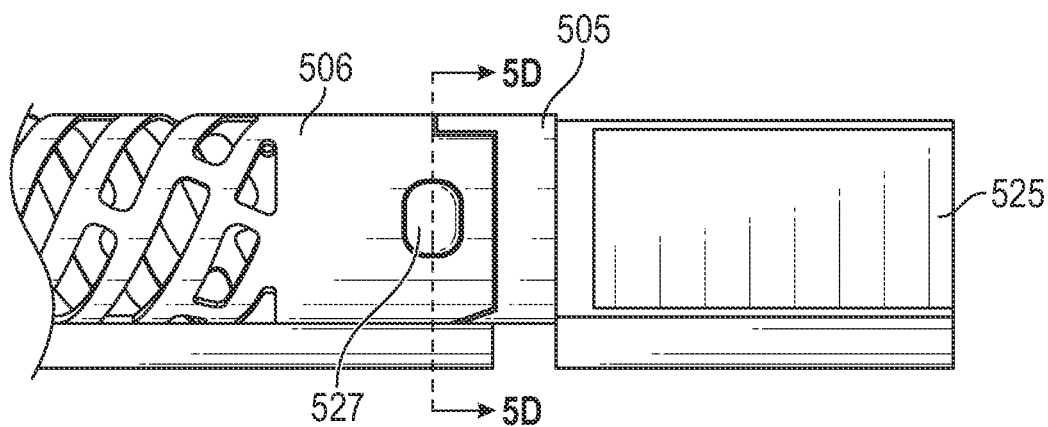
FIG. 5C shows a close-up of the nosecone of FIG. 5A in the locked position with the distal portion of the nosecone removed for clarity.
Figure 5D:
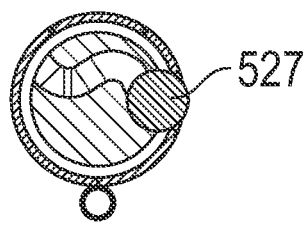
FIG. 5D shows a cross-section through the locked nosecone shown in FIG. 5C.
Figure 5E:
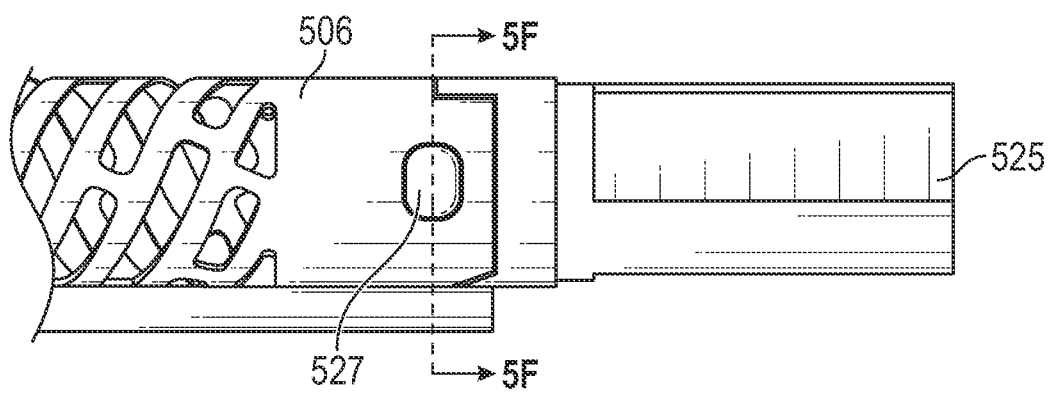
FIG. 5E shows a close-up of the nosecone of FIG. 5A in the unlocked position with the distal portion of the nosecone removed for clarity.
Figure 5F:
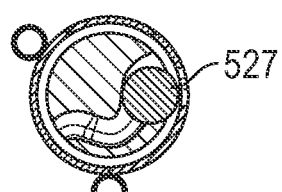
FIG. 5F shows a cross-section through the unlocked nosecone shown in FIG. 5E.

Another exemplary embodiment of a nosecone 504 is shown in FIGS. 5A-5H. As shown in FIG. 5A, the nosecone 504 includes a proximal end 506 and a detachable distal end 505. The nosecone 504 further includes a coupling mechanism 515 configured to allow for attachment and detachment of the distal end 505 of the nosecone 504. Referring to FIGS. 5B and 5G, the coupling mechanism 515 includes a solid plug 571 that fits within, and seals to, the inner diameter of the proximal end 506 of the nosecone 504. The coupling mechanism 515 further includes an annular collar 573 configured to permanently attach to the proximal end 506 of the nosecone. The coupling mechanism 515 connects together by twisting a rotatable tab 525 (which is fixed to the collar 573) to activate a cam 577. When the distal end 505 is locked to the proximal end 506 (as shown in FIGS. 5C and 5D), a ball bearing 527 sits within an outer window 533. When unlocked, however, the ball bearing 527 is pulled back inside the window 533 into the inner slot 531 (as shown in FIGS. 5E-5F).

In use, the user can grab the tab 525 (e.g., through a flexible portion of the distal end 505), insert the plug 571 into the distal end 505, and rotate the tab 525. As shown in FIG. 5G, doing so will cause the peak in the cam 577 to push the ball 527 from the window 531 towards the window 533. Once engaged in the window 533, the ball 527 will prevent future movement of the proximal and distal ends 506, 505 relative to one another. To unlock, the user can rotate the tab 525 in the opposite direction. This will cause the ball 527 to move all the way back into the inner window 531, allowing the distal end 505 to be pulled distally away from the proximal end 506.

The coupling mechanism 515 is positioned close to the distal tip of the nosecone 504 (e.g., 1-2 inches, such as approximately 1.5 inches away from the distal edge of the cutting window 507). This can advantageously provide for ample room for tissue packing inside the proximal portion 506 and prevent interference of the coupling mechanism 515 with the cutter as it packs tissue.

Figure 6C:
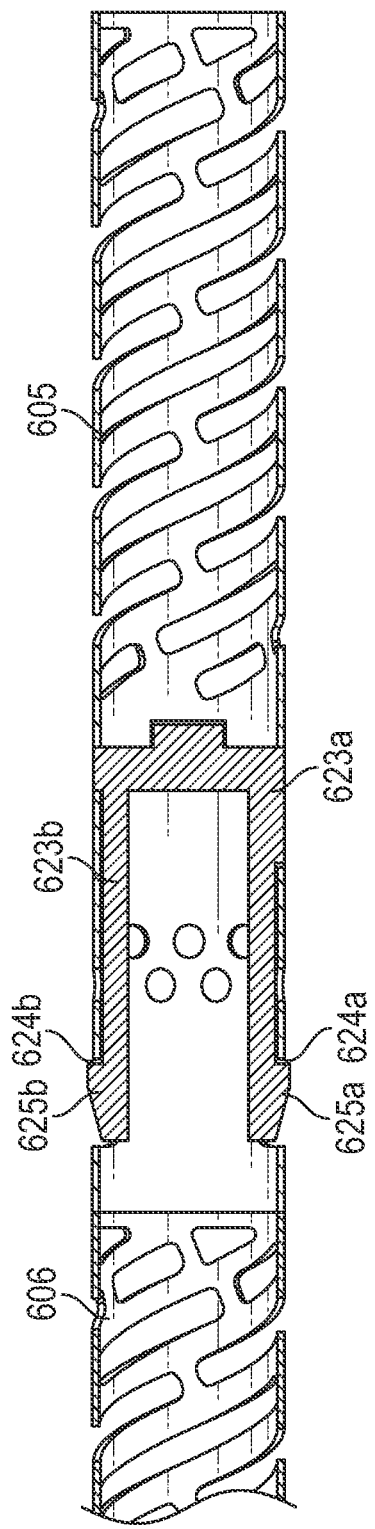
FIG. 6C is a cross-section showing the proximal and distal ends connected.

Another exemplary embodiment of a nosecone 604 is shown in FIGS. 6A-6C. The nosecone 604 includes a proximal end 606 and a detachable distal end 605. The nosecone 604 further includes a coupling mechanism 622 configured to allow for attachment and detachment of the distal end 605 from the proximal end 606. The coupling mechanism 622 includes a solid plug that fits within, and seals to, the inner diameter of the proximal end 606 of the nosecone. The coupling mechanism 622 further includes two snap arms 623a,b that extend proximally away from the plug. The snap arms 623a,b can further include radially extending tabs 625a,b that are configured to snap into corresponding snap window 624a,b on the proximal end 606. In some embodiments, the user can release the distal end 605 by pushing on the tabs 625a,b. Further, in some embodiments, the tabs 625a,b can be chamfered at one edge such that either clockwise or counterclockwise rotation can automatically push the tabs 625a,b to release the coupling mechanism 622.

Again, the coupling mechanism 622 is positioned close to the distal tip of the nosecone 604 (e.g., there can be about 1-2 inches, such as 1.5 inches, from a distal edge of the cutter window 607 to a proximal end of the snap arms). This can advantageously provide for ample room for tissue packing inside the proximal portion 606 and prevent interference of the coupling mechanism 622 with the cutter as it packs tissue.

Figure 7:
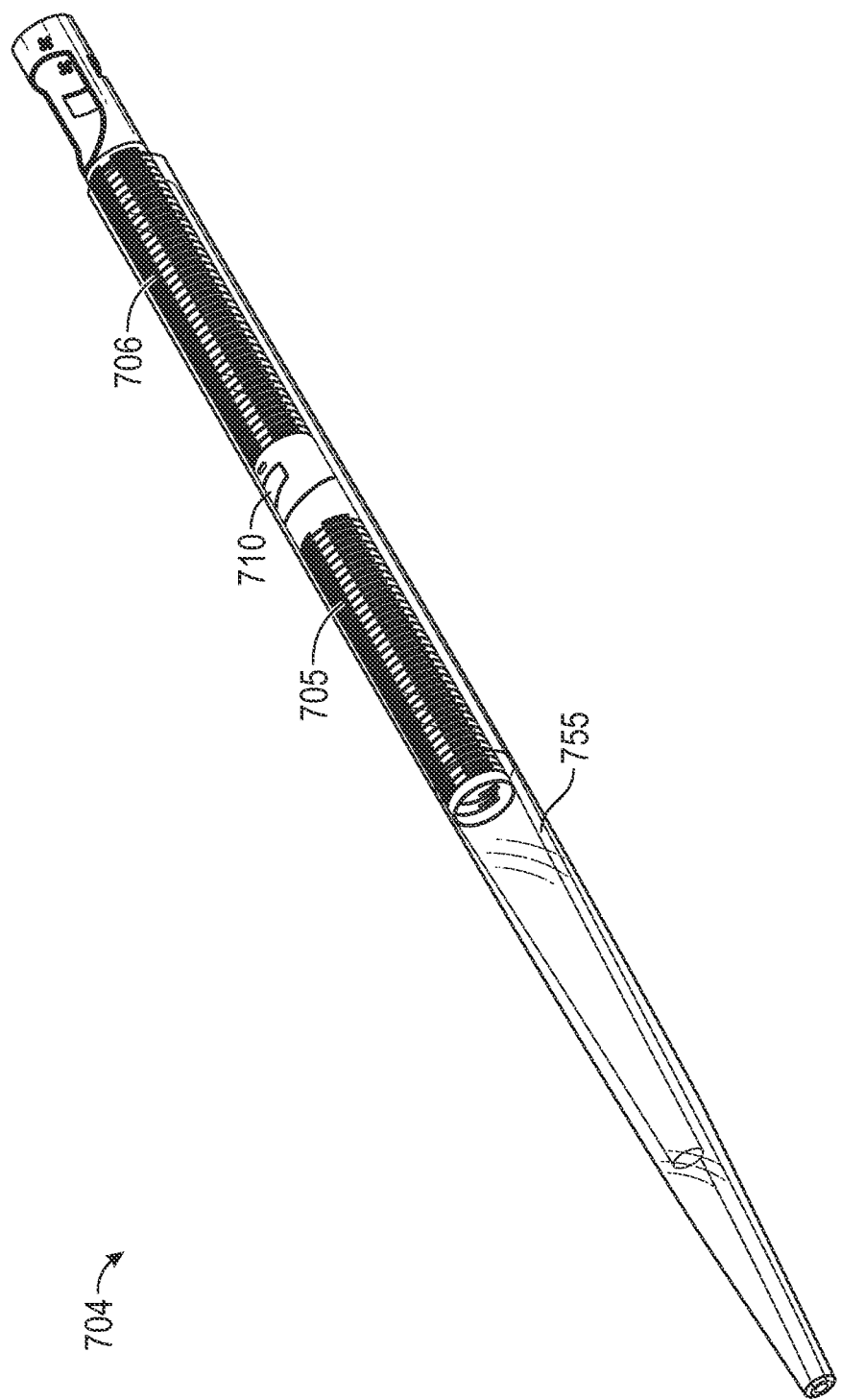
FIG. 7 shows a separable nosecone with monorail guidewire lumen.

Referring to FIG. 7, in any of the embodiments described herein, a guidewire lumen 755 can extend down the side of the nosecone 704. The guidewire lumen 755 can include two interconnectable sections (one section attached to the proximal end 706 and another section attached to the distal end 705). Insertion of the guidewire through the lumen 755 can help keep the proximal and distal ends 706, 705 of the nosecone together. That is, the insertion of the guidewire through the lumen 755 can help prevent rotation of the proximal and distal ends 706, 705 relative to one another when a rotatable or twisting locking mechanism 710 is used to unlock (e.g., any of the embodiments described herein that include twisting or rotation to unlock).

In some embodiments, features on both the nosecone distal end and the nosecone proximal end may aid a user in properly aligning the nosecone proximal end with the nosecone distal end. For example, in some instances, the nosecone proximal end and the nosecone distal end may be angled or biased such that they fit together. To further ensure proper alignment or attachment of these two components, the nosecone proximal end and the catheter distal end may further include features on the angled or biased end surfaces that are configured to mate. In other examples, there may be visual indicators on the nosecone proximal end and the catheter body distal end that aid a user in aligning the two portions.

In some embodiments, the attachment features can include an auditory or physical signal that indicates that the proximal and distal ends of the nosecone are connected (e.g., the detent feature can make a clicking noise to signal locking).

In some embodiments, the attachment mechanisms and distal ends of the nosecones described herein can be reusable. In other embodiments, the distal end of the nosecone is meant as a single use, and the attachment mechanisms cannot be detached and then reattached. For example, the tab features can be configured to break or become unusable after disengaged.

The attachment mechanisms shown with respect to FIGS. 3A-6C have a substantially smooth inner circumference (i.e., on the inside of the nosecone) and are free of tabs or mechanisms that extend radially inwards into the nosecone. This can advantageously prevent the attachment mechanisms from interfering with the movement of the cutter as it is moved into the nosecone (i.e., for packing) and/or prevent pieces of excised plaque or tissue from becoming entangled on radially inwardly protruding extensions of the attachment mechanisms.

In some embodiments, the nosecone attachment mechanisms described herein are a set distance from the cutting window to further eliminate interference with the cutter. Thus, the distance between the attachment mechanism and the cutting window can be, for example, 0.5"-1.0", such as 0.6"-0.8", such as approximately 0.68" or 0.70". In some embodiments, the distal edge of the cutter, when fully extended, can be positioned just proximal of the attachment mechanisms.

It should be understood that any suitable mechanism or means (e.g. friction fit, mated fit, threaded fit, hooks, securing members, etc.) may be used in addition to, or in place of, the attachment mechanisms described herein to detach a portion or the entirety of a tissue collection device to another device.

Additionally, any suitable materials such as nitinol, stainless steel (e.g. grade 304), or titanium or alloys may be used to form the attachment mechanisms. Coatings including gold or platinum may be used to promote radiopacity.

Any of the features of the described tissue collection devices can be used in combination without departing from the disclosure.

Having a nosecone with detachable sections therein can advantageously be used for flushing or otherwise clearing excised tissue out of the nosecone. That is, after tissue has been excised and collected in the nosecone (such as by packing it into the nosecone through axial movement of the cutter), the distal end or section of the nosecone can be removed, thereby permitting the proximal end to be flushed (e.g., from the cutting window through the open distal end) and/or allowing either the proximal or the distal end to be easily cleared with a tissue removal tool.

Although the above coupling mechanisms have been described as being used to attach and detach to portions of a nosecone, they can also be used to couple other portions of a catheter. For example, in some embodiments, the entire tissue-collection portion of the nosecone can be removable from the rest of the catheter using one of the coupling mechanisms described herein.

Any of the described tissue collection devices can be used with atherectomy or other occlusion crossing devices. In such cases, the atherectomy devices typically include an elongate body and a rotatable tip (with a cutter) at the first distal end of the elongate body and configured to rotate relative to the elongate body. Such devices are described in U.S. Patent Application No. 61/646,843, titled "ATHERECTOMY CATHETERS WITH IMAGING," filed on May 14, 2012, U.S. patent application Ser. No. 13/433,049, titled "OCCLUSION-CROSSING DEVICES, IMAGING, AND ATHERECTOMY DEVICES," filed Mar. 28, 2012, U.S. patent application Ser. No. 13/175,232, titled "ATHERECTOMY CATHETERS WITH LONGITUDINALLY DISPLACEABLE DRIVE SHAFTS," filed on Jul. 1, 2011, U.S. patent application Ser. No. 12/829,277, titled "ATHERECTOMY CATHETER WITH LATERALLY-DISPLACEABLE TIP," filed on Jul. 1, 2010, and U.S. patent application Ser. No. 12/829,267, titled "CATHETER-BASED OFF-AXIS OPTICAL COHERENCE TOMOGRAPHY IMAGING SYSTEM," filed on Jul. 1, 2010, International Patent Application No. PCT/US2015/014613, titled "ATHERECTOMY CATHETERS AND OCCLUSION CROSSING DEVICES," filed on Feb. 5, 2015, U.S. patent application Ser. No. 15/072,272, titled "ATHERECTOMY CATHETERS DEVICES HAVING MULTI-CHANNEL BUSHINGS," filed on Mar. 16, 2016, and U.S. patent application Ser. No. 15/076,568, titled "ATHERECTOMY CATHETERS AND OCCLUSION CROSSING DEVICES," filed on Mar. 21, 2016, all of which are herein incorporated by reference in their entirety.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An atherectomy catheter comprising:
    a catheter body having a catheter body proximal end, a catheter body distal end, a cutting window, and a cutter exposable through the cutting window;
    a nosecone having a nosecone proximal end and a nosecone distal end, wherein the nosecone proximal end is configured to couple and decouple from the nosecone distal end; and
    a collar having a collar inner surface configured to maintain a detachable connection between the nosecone proximal end with the nosecone distal end.

2. The atherectomy catheter of claim 1, wherein the nosecone further comprises a hollow interior portion configured to receive excised tissue.

3. The atherectomy catheter of claim 1, wherein the nosecone is rigid.

4. The atherectomy catheter of claim 1, wherein the nosecone is flexible.

5. The atherectomy catheter of claim 1, wherein the nosecone comprises both flexible and rigid regions.

6. The atherectomy catheter of claim 1, further comprising a guidewire channel disposed on the nosecone and the catheter body.

* * * * *